(12) United States Patent
Yang

(10) Patent No.: US 9,034,582 B2
(45) Date of Patent: May 19, 2015

(54) METHOD FOR DETECTING THE RISK OF ALZHEIMER'S DISEASE BY DETECTING IMMUNOMAGNETIC REDUCTION SIGNALS OF BIOLOGICAL MARKERS

(71) Applicant: MagQu Co. Ltd., New Taipei (TW)

(72) Inventor: Shieh-Yueh Yang, New Taipei (TW)

(73) Assignee: MAGQU CO. LTD., New Taipei (TW)

( * ) Notice: Subject to any disclaimer, the term of this patent is extended or adjusted under 35 U.S.C. 154(b) by 0 days.

(21) Appl. No.: 14/200,020

(22) Filed: Mar. 7, 2014

(65) Prior Publication Data
US 2014/0370518 A1 Dec. 18, 2014

(30) Foreign Application Priority Data
Jun. 18, 2013 (TW) .............................. 102211361 U

(51) Int. Cl.
- G01N 33/68 (2006.01)
- G01N 27/74 (2006.01)
- G01N 33/543 (2006.01)
- G06F 19/00 (2011.01)

(52) U.S. Cl.
CPC .......... *G01N 33/6896* (2013.01); *G01N 27/745* (2013.01); *G06F 19/34* (2013.01); *G01N 33/54326* (2013.01)

(58) Field of Classification Search
None
See application file for complete search history.

(56) References Cited

FOREIGN PATENT DOCUMENTS

EP 1535930 * 6/2010 ............. C07K 16/18

OTHER PUBLICATIONS

Chiu et al. 2012 "New assay for old markers-plasma beta amyloid of mild cognitive impiarment and Alzheimer's disease" Curr Alz Res 9(10):1142-8 (abstract only).*
Fawcett 2006 "An introduction to ROC analysis" Pattern Recognition Letters 27:861-874.*
GIM 2001 "The Area under an ROC curve" downloaded from http://gim.unmc.edu on Jul. 9, 2014.*
Hanley and McNeil 1983 "A method of comparing the areas under receiver operating characteristic curves derived from the same cases" Radiology 148(3):839-43 (abstract only).*
Ibach et al. 2005 "cerebrospinal fluid tau and β-amyloid in Alzheimer patients, disease controls and an age-matched random sample" Neuro Biol Aging 27(9):1202-11 (abstract only).*
Mason and Graham 2002 "areas beneath the relative operating characteristics (ROC) and relative operating levels (ROL) curves: Statistical significance and interpretation" QJR Meteorol Soc 128:2145-2166 (abstract only).*
Mulder et al. 2010 "amyloid β(1-42), total tau, and phosphorylated tau as cerebrospinal fluid biomarkers for the diagnosis of alzheimer's disease" Clinical Chemistry 56(2):248-253.*
Parnetti et al. 2012 "Performance of aβ1-40, aβ1-42, total tau, and phosphorylated tau as predictors of dementia in a cohort of patients with mild cognitive impairment" JAD 29(1):229-38 (abstract only).*
Senanarong et al. 2012 "Alzheimer's disease dementia as the diagnosis best suppoerted by the cerebrospinal fluid biomarkers: difference in cut-off levels from thai experience" International JAD 2012:1-5.*
Yang et al. 2011 "Biofunctionalized magnetic nanoparticles for specifically detecting biomarkers of Alzheimer's disease in vitro" ACS chem neurosci 2:500-505.*
Chiu et al. 2013 "Combined plasma biomarkers for diagnosing mild cognition impairment and Alzheimer's disease" ACS chemical neuroscience 4:1530-1536.*
C. C. Yang et al., Effect of molecule-particle binding on the reduction in the mixed-frequency alternating current magnetic susceptibility of magnetic bio-reagents, Journal of Applied Physics, vol. 112, Issue 2, 2012.

* cited by examiner

Primary Examiner — Gregory S Emch
Assistant Examiner — Adam M Weidner
(74) Attorney, Agent, or Firm — Hannah M. Tien

(57) ABSTRACT

A method for detecting the risk of Alzheimer's disease comprises detecting immunomagnetic reduction signals of two biological markers in a biological sample from a subject, wherein the two biological markers are tau protein and Aβ-42 protein; and calculating concentrations of the above two biological markers and using the product of the concentrations of the above two biological markers to diagnose the risk of Alzheimer's disease, wherein the concentration is calculated by the conversion of the magnetic reduction signals.

7 Claims, 7 Drawing Sheets

(a)

(b)

(a)

(b)

(c)

(a)

(b)

(c)

(a)

(b)

(c)

METHOD FOR DETECTING THE RISK OF ALZHEIMER'S DISEASE BY DETECTING IMMUNOMAGNETIC REDUCTION SIGNALS OF BIOLOGICAL MARKERS

CROSS-REFERENCES TO RELATED APPLICATIONS

The present application claims priority to TW 102211361, filed Jun. 18, 2013 incorporated herein by reference in its entirety.

BACKGROUND OF THE INVENTION

1. Field of the Invention

The present invention relates to a method for detecting risk of Alzheimer's disease by using immunomagnetic reduction (IMR) assays of the product of the concentrations of tau protein and Aβ-42 protein, two biomarkers for Alzheimer's disease.

2. Description of Prior Art

Due to rapid aging of the global population, neurodegenerative diseases become serious problems nowadays. Dementia is the most prevalent neurodegenerative disease among them all. In most regions of the world the prevalence rate of dementia among the elderly over the age of 60 is 5-7%. It was projected that close to 35.6 million people worldwide would suffer from dementia in 2010. The World Health Organization has urged that all governments, policy-makers and other stakeholders should view the impact of dementia as an increasing threat and should allocate all necessary resources to make medical and social care systems ready for the imminent threat of dementia.

Patients with Alzheimer's disease (AD) comprise 50%-70% of the elderly population suffering from dementia. Neuroimaging and neurocognitive tests are two cornerstones of the current medical practice used to diagnose Alzheimer's disease. Although neurocognitive tests are easier to implement as compared to neuroimaging, the results depend not only on the degree of neurodegeneration but also on other factors such as education, cultural background, social economic status, etc. Hence, care must be taken when patients are assessed by neurocognitive tests and the test results should not be the only information to reach a final diagnosis of Alzheimer's disease. As for neuroimaging, structural or functional data can be obtained to diagnose Alzheimer's disease on an objective ground. For example, hippocampal atrophy can be identified either qualitatively (visual rating) or quantitatively (volumetry) by using magnetic resonance imaging; and amyloid or tau positron emission tomography (PET) can show amyloid plaques and neurofibrillary tangles typically found in the brains of Alzheimer's disease patients. However, neuroimaging is expensive and generally not accessible, especially in private clinics or small hospitals. Therefore, people are motivated to develop other technologies for diagnosing Alzheimer's disease.

Molecular diagnosis is the new trend of in-vitro diagnosis of Alzheimer's disease. The potential biomarkers include amyloids, tau protein, and their derivates. Most of these biomarkers are found in cerebrospinal fluid (CSF). Lumbar puncture is necessary in order to collect CSF samples. Since the CSF sampling process is relatively risky and discomfort, CSF samples are not suitable for screening Alzheimer's disease on a large scale, nor are they suitable for monitoring of disease prognosis or therapeutic effect on a long term basis which requires repetitive samplings. Therefore, biomarkers in body fluids other than CSF have been sought. One of the most promising body fluids is blood which the most reliable, convenient and familiar clinical sample. However, the concentrations of biomarkers in blood are very low, so low that they are expressed at the level of pg/ml. Ultra-high-sensitivity assay technologies are needed for the detection of these ultra-low-concentration biomarkers.

An ultra-high-sensitivity technology for immunoassay had been developed in 2008. This technology is now referred to as superconducting quantum interference device (SQUID) immunomagnetic reduction (IMR) assays. The low-detection limits of the SQUID based IMR for amyloids and tau protein were found to be 1-10 pg/ml, which made the measurement of plasma biomarkers for diagnosing Alzheimer's disease possible. Hence, the present invention discloses the characterizations of SQUID IMR for assaying biomarkers in human plasma.

SUMMARY OF THE INVENTION

The present invention provides a method for detecting risk of Alzheimer's disease, comprising: (a) detecting in vitro immunomagnetic reduction (IMR) signals of two Alzheimer's disease biomarkers in a biological sample of a subject, wherein the IMR signals are produced by the two Alzheimer's disease biomarkers binding with magnetic nanoparticles containing an anti-Alzheimer's disease biomarker antibody, wherein the two Alzheimer's disease biomarkers are tau protein and Aβ-42 protein respectively; (b) the IMR signals of the two Alzheimer's disease biomarkers detected in step (a) are fitted to a logistic function (I) to calculate each Alzheimer's disease biomarker's concentration in the biological sample:

$$IMR(\%) = \frac{A-B}{1+\left(\frac{\phi}{\phi_o}\right)^\gamma} + B \quad (I)$$

wherein IMR(%) is the IMR signals of a biomarker, $\phi$ is the concentration of the Alzheimer's disease biomarker, fitting parameter A is a background value, B is a maximum value, $\phi_o$ is the concentration of the biomarker when IMR signal equals ((A+B)/2), $\gamma$ is a slope at data point $\phi_o$ of a curve where $\phi$ is x-axis and IMR(%) is y-axis; and (c) comparing a product of the two Alzheimer's disease biomarkers' concentration obtained in step (b) to a standard value calculated by multiplying two Alzheimer's disease biomarkers' concentrations, when the product of two Alzheimer's disease biomarkers' concentration is higher than the standard value that is indicative of the increasing risk of Alzheimer's disease of the subject.

DETAILED DESCRIPTION OF THE INVENTION

Figure 1:
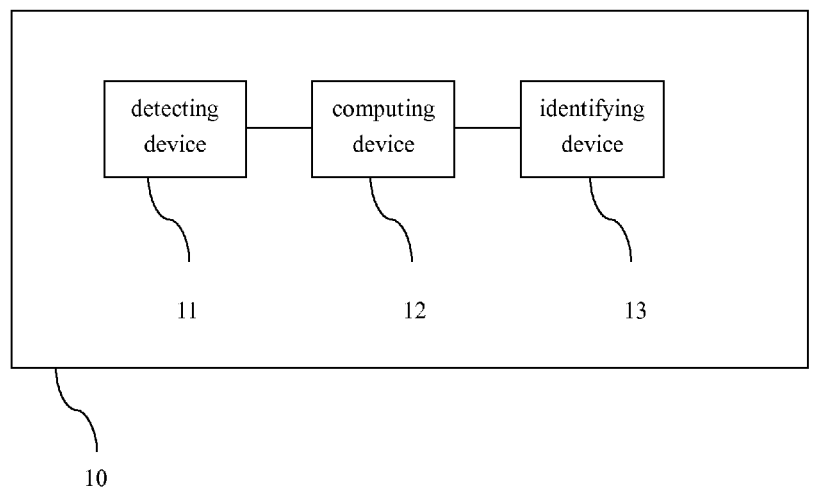
FIG. 1 illustrates the detection system 10 of the present invention.

The present invention provides a system 10 (FIG. 1) for detecting the risk of Alzheimer's disease (AD), comprising:
a detecting device 11, which is used to detect immunomagnetic reduction (IMR) signals which are produced when two biomarkers in a biological sample from a subject bind with magnetic nanoparticles containing anti-Alzheimer's disease biomarker antibody, wherein the two biomarkers are tau protein and Aβ-42 protein respectively;
a computing device 12, which is connected with the detecting device 11 to receive the IMR signals of the two Alzheimer's disease biomarkers and to calculate concentration of each of two biomarkers in the biological sample by fitting to the logistic function (I)

$$IMR(\%) = \frac{A - B}{1 + \left(\frac{\phi}{\phi_o}\right)^{\gamma}} + B \quad (I)$$

wherein, IMR (immunomagnetic reduction) is the IMR signal of a biomarker, $\phi$ is the individual concentration of the biomarker for Alzheimer's disease, fitting parameter A is background value, B is a maximum value, $\phi_0$ is the concentration of the biomarker when IMR signal equals ((A+B)/2), and $\gamma$ is the slope of a curve at data point $\phi_0$ where $\phi$ is the x-axis and IMR (%) is the y-axis of the curve; and
an identifying device 13, which is connected with the computing device 12 to calculate a product of the two Alzheimer's disease biomarkers' concentrations calculated by the computing device 12 and to determine the risk of Alzheimer's disease based on the product of the two Alzheimer's disease biomarkers' concentrations.

In one embodiment, the Alzheimer's disease is Alzheimer's disease dementia (ADD). In a preferred embodiment, the Alzheimer's disease dementia includes cognitive impairments due to Alzheimer's disease. In another preferred embodiment, the cognitive impairment due to Alzheimer's disease is mild cognitive impairment (MCI) due to Alzheimer's disease.

In one embodiment, the identifying device 13 determines the risk of Alzheimer's disease by comparing the product of two Alzheimer's disease biomarkers' concentrations in a biological sample of a subject to a predetermined threshold (or cut-off value) which is a product of two Alzheimer's disease biomarkers' concentrations calculated by using a receiver operating characteristic (ROC) curve; the subject's risk of suffering from Alzheimer's disease increases when the product is higher than the predetermined threshold. In a preferred embodiment, the predetermined threshold of two Alzheimer's disease biomarkers' concentrations is determined by a data point of the highest specificity at the highest sensitivity on the ROC curve, wherein the ROC curve is plotted according to the products calculated by multiplying two Alzheimer's disease biomarkers' concentrations of subjects from both the healthy control group and the Alzheimer's disease patient group.

In one embodiment, the highest sensitivity ranges from 0.7 to 1. In another embodiment, the highest specificity ranges from 0.7 to 1.

In one embodiment, the computing device and the identifying device are integrated into an integrated circuit.

In another embodiment, the biological sample is blood sample. In a preferred embodiment, the blood sample is plasma.

Figure 2:
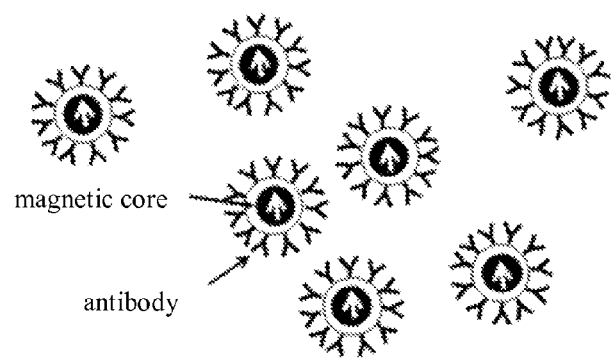
FIG. 2 (a) illustrates the detection reagent of the present invention. (b) shows the biomarker-bonded detection reagent.
Figure 2:
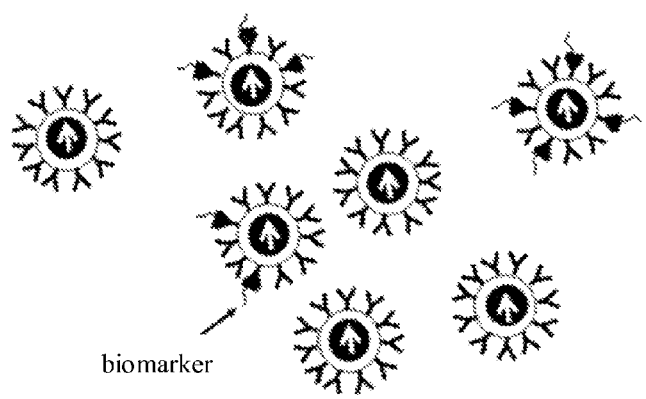

The present invention further provides a reagent for detecting Alzheimer's disease, comprising a plurality of magnetic nanoparticles dispersed in solution, wherein the structure of a magnetic nanoparticle comprises (FIG. 2 (a)):
a magnetic core; and
a water soluble material covering on the magnetic core; and
an antibody, attaching to the water soluble material outside of the magnetic core, which is used to identify biomarkers in a biological sample.

In one embodiment, the antibody is an antibody of an anti-Alzheimer's disease biomarker. In a preferred embodiment, the antibody of the anti-Alzheimer's disease biomarker is an antibody of anti-tau protein or an antibody of anti-Aβ-42 protein.

In one embodiment, material of the magnetic core is selected from a group consisting of $Fe_3O_4$, $Fe_2O_3$, $MnFe_2O_4$, $CoFe_2O_4$, $NiFe_2O_4$. In a preferred embodiment, the material of the magnetic core is $Fe_3O_4$.

In another embodiment, the biomarker in the biological sample is tau protein or Aβ-42 protein which is capable of being bonded with the antibody conjugated with the magnetic nanoparticles. (FIG. 2 (b))

The present invention further provides a method for diagnosing Alzheimer's disease, comprising:
providing the above reagent for detecting Alzheimer's disease;
providing a biological sample;
detecting IMR signal of a biomarker after mixing the biological sample with the reagent; and
comparing the IMR signal detected in the biological sample to a IMR signal standard curve of the biomarker.

In one embodiment, the IMR signal standard curve of the biomarker is Aβ-42 protein or tau protein concentration-dependent curve, including a data point of the peak IMR signal. In a preferred embodiment, the IMR signal standard curve of the biomarker is an IMR (%)-$\phi$ curve or a characteristic curve.

In another embodiment, the data points of the biomarker's IMR signals are fitted by using a logistic function (I):

$$IMR(\%) = \frac{A - B}{1 + \left(\frac{\phi}{\phi_o}\right)^\gamma} + B \quad (I)$$

wherein, A, B, $\phi_o$ and $\gamma$ are fitting parameters, A is a background value, B is a maximum value, $\phi_o$ is the concentration of the biomarker when IMR signal equals ((A+B)/2), and $\gamma$ is a slope of a curve where $\phi$ is x-axis and IMR (%) is y-axis, the fitting curve of the biomarker is plotted according to the logistic function, and the data can be further analyzed by the ROC curve.

The present invention further provides a method for detecting risk of Alzheimer's disease, comprising: (a) detecting in vitro immunomagnetic reduction (IMR) signals of two Alzheimer's disease biomarkers in a biological sample of a subject, wherein the IMR signals are produced by the two Alzheimer's disease biomarkers binding with magnetic nanoparticles containing an anti-Alzheimer's disease biomarker antibody, wherein the two Alzheimer's disease biomarkers are tau protein and Aβ-42 protein respectively; (b) the IMR signals of the two Alzheimer's disease biomarkers detected in step (a) are fitted to a logistic function (I) to calculate each Alzheimer's disease biomarker's concentration in the biological sample:

$$IMR(\%) = \frac{A - B}{1 + \left(\frac{\phi}{\phi_o}\right)^\gamma} + B \quad (I)$$

wherein IMR (%) is the IMR signals of a biomarker, $\phi$ is the concentration of the Alzheimer's disease biomarker, fitting parameter A is a background value, B is a maximum value, $\phi_o$ is the concentration of the biomarker when IMR signal equals ((A+B)/2), $\gamma$ is a slope at data point $\phi_o$ of a curve where $\phi$ is x-axis and IMR (%) is y-axis; and (c) comparing a product of the two Alzheimer's disease biomarkers' concentration obtained in step (b) to a standard value calculated by multiplying two Alzheimer's disease biomarkers' concentrations, when the product of two Alzheimer's disease biomarkers' concentration is higher than the standard value that is indicative of the increasing risk of Alzheimer's disease of the subject.

As used herein, the logistic function (I) mentioned in the present invention refers to the formula used to convert IMR signals into concentrations and disclosed by prior art (C. C. Yang et al., Effect of molecule-particle binding on the reduction in the mixed-frequency alternating current magnetic susceptibility of magnetic bio-reagents, Journal of Applied Physics, Volume 112, Issue 2, 2012). When using the logistic function (I), a graphs is plotted where the concentration of the standard biomarker is the x-axis and the corresponding IMR signal is the y-axis; the background value (A) is then determined by detecting the IMR signal of a reagent free from a daitse biomarker; the maximum value (B) is determined by detecting the IMR signal of the reagent which is saturated with the daitse biomarker; a curve between points A and B is drawn on the graphs, the concentration of the biomarker ($\phi_o$) is a point on the curve where the IMR signals equals to ((A+B)/2); calculating the slope ($\gamma$) at $\phi_o$; and the concentration of the to-be-detected biomarker ($\phi$) can then be computed.

As used herein, the term "ROC" means "receiver operating characteristic" and refers to a method of concentration analysis. A ROC analysis is used to evaluate the diagnostic performance of a test. A ROC graph is a plot of sensitivity (%) and specificity (%) of a test at various thresholds or cut-off values. An ROC curve may be used to differentiate between two sample groups, such as a control or normal sample having specified characteristics, and a test or experimental sample. Usually the distributions seen in the two samples will overlap, making it a non-trivial exercise to determine whether there is a real difference between them. If the discrimination threshold or specificity of a ROC analysis is set at high, then the test is less likely to generate a false positive, i.e. less likely wrongly identify a difference between the two samples. However, in these circumstances the test will be more likely to miss instances where there is a real difference between the samples and consequently it is more likely that some cases of disease will not be identified. If the sensitivity of the test is increased, there is a corresponding fall in specificity. Thus if the test is made more sensitive then the test is more likely to identify most or all of the subject with the disease, but will also diagnose the disease in more subject who do not have the disease.

Each point on a ROC curve represents the sensitivity and its respective specificity. A threshold concentration can be selected based on an ROC curve to identify a point where sensitivity and specificity both have acceptable values, and this point can be used in applying the test for diagnostic purposes. While a user is able to modify the parameters in ways that will be readily understood by those skilled in the art, for the examples described in this disclosure each threshold or cut-off concentration is chosen to obtain both reasonable sensitivity and specificity. In particular instances both of these were maintained at approximately 60% to 95%, although lower and higher values are possible.

Another useful feature of the ROC curve is an area under the curve (AUC) value, which quantifies the overall ability of the test to discriminate between different sample properties, in this case to discriminate between those subjects with Alzheimer's disease and those without Alzheimer's disease. A test that is no better at identifying true positives than random chance will generate a ROC curve with an area of 0.5. A test having perfect specificity and sensitivity, generating no false positives and no false negatives, will have an area of 1.00. In reality, any test will have an area somewhere between these two values.

In one embodiment of the present invention, a ROC curve is plotted according to the products of the concentrations of two Alzheimer's disease biomarkers (tau protein and Aβ-42 protein) detected in blood samples of Alzheimer's disease patients and healthy individuals. A plot is thus generated, which can be used to determine the sensitivity (%) and specificity (%) of the corresponding products of two Alzheimer's disease biomarkers' concentrations at various threshold or cut-off concentrations. The use of ROC analysis is readily understood and can be easily implemented by those skilled in the art.

In one embodiment, the ROC curve is plotted using 1-specificity as the x-axis and sensitivity as the y-axis.

As used herein, the term "sensitivity" refers to the percentage of correct identification as subjects suffering from Alzheimer's disease using concentration products of two Alzheimer's disease biomarkers (tau protein and Aβ-42 protein). In other words, sensitivity is equal to (true positive result)/[(true positive result)+(false negative result)].

As used herein, the term "specificity" refers to the percentage of correct identification as healthy subjects of a control group. In other words, specificity is equal to (true negative result)/[(true negative result)+(false positive result)].

In one embodiment, the standard value calculated by multiplying two Alzheimer's disease biomarkers' concentration is a threshold or cut-off value determined by the ROC curve. In a preferred embodiment, the threshold is determined by a point of the highest specificity at the highest point of sensitivity.

In one embodiment, the range of the highest sensitivity is from 0.7 to 1. In another embodiment, the range of the highest specificity is from 0.7 to 1.

In one embodiment, the threshold is further determined by the maximum area under the ROC curve (AUC). In a preferred embodiment, the maximum area ranges from 0.7 to 1.

As used herein, the term "subject" refers to a mammal, preferably a human. The mammals include, but are not limited to, humans, primates, livestock, rodents, and pets.

As used herein, the term "patient" refers to a person who is under or in need of medical care or treatment. The person may be waiting for the medical care or treatment, may be under the medical care or treatment, or may have been received the medical care or treatment.

As used herein, the term "healthy control group," "normal group" or a sample from a "healthy" individual means a person who is diagnosed by a physician as not suffering from Alzheimer's disease based on qualitative or quantitative test results. A "normal" individual is usually about the same age as the individual to be evaluated, including, but not limited, individuals of the same age. The age error is within the range of 5 to 10 years.

In one embodiment, the ROC curve is plotted according to the products of the two Alzheimer's disease biomarkers' concentrations of subjects from both a Alzheimer's disease patient group and a healthy control group In one embodiment, the Alzheimer's disease is Alzheimer's disease dementia. In a preferred embodiment, the Alzheimer's disease dementia includes cognitive impairments due to Alzheimer's disease. In another preferred embodiment, the cognitive impairment due to Alzheimer's disease is mild cognitive impairment due to Alzheimer's disease.

In one embodiment, material of magnetic nanoparticles is selected from a group consisting of $Fe_3O_4$, $Fe_2O_3$, $MnFe_2O_4$, $CoFe_2O_4$, and $NiFe_2O_4$. In a preferred embodiment, the material of magnetic nanoparticles is $Fe_3O_4$.

As used herein, the term "blood sample" refers to a biological sample derived from blood, preferably peripheral (or circulating) blood. The blood sample can be whole blood, plasma or serum. In another embodiment, the biological sample is blood sample. In a preferred embodiment, the blood sample is plasma.

Compared to other techniques, the method for determining risk of Alzheimer's disease provided by the present invention has the following advantages:
(1) The IMR assays allow the present invention to use blood sample as the biological sample, which is relatively easier and safer to collect as compared to cerebrospinal fluid. By using IMR assays the concentrations of Alzheimer's disease biomarkers, for example tau protein and Aβ-42 protein, can be sensitively detected at the level of pg/ml, a level that other immunoassay technologies cannot provide.
(2) The sensitivity and specificity of Aβ-42 protein is poor when it is used individually as a biomarker to identify Alzheimer's disease. The concentration of tau protein rises whenever there is a brain damage, which makes tau protein a poor biomarker to identify Alzheimer's disease because of its low specificity. The present invention provides a new Alzheimer's disease-identifying parameter, the product of two Alzheimer's disease biomarkers' concentrations, which is capable of differentiating mild cognitive impairments due to Alzheimer's disease from Alzheimer's disease dementia with high sensitivity and specificity. The present invention can diagnose mild cognitive impairment at the pre-clinical stage of Alzheimer's disease.

EXAMPLES

The essence of the present invention is to detect the risk of Alzheimer's disease by using the product of the concentrations of tau protein and Aβ-42 protein, which are two Alzheimer's disease biomarkers (AD biomarkers). The examples below are non-limiting and are merely representative of various aspects and features of the present invention.

According to the clinical dementia rating scale (CDR), the plasma samples were collected from 66 healthy individuals and 61 patients suffering from AD dementia of various severity, from very mild (CDR 0.5), mild (CDR 1) to severe (CDR 3), for assays of amyloids and tau protein using SQUID IMR. All of the patients suffering from dementia met the diagnostic guidelines published by the US National Institute on Aging-Alzheimer's Association (NIA-AA) workgroups in 2011. The control subjects were selected from a group of healthy volunteers in an MCI cohort project.

In the prodromal stage of AD, patients usually suffer from mild cognition impairment (MCI). The annual conversion rate of MCI to AD is about 10% and within three years about 30 to 50% of them become dementia. In a subgroup of cerebral amyloid positive MCI, the three-year accumulated conversion rate may go up to 82%. To implement possible preventive intervention for Alzheimer's disease dementia, MCI due to AD need to be diagnosed by biomarker assays as early as possible. Hence, plasma samples of 24 patients with MCI due to AD were analyzed for amyloids and tau protein using SQUID IMR. The diagnosis of MCI due to AD also followed the recommendations from the NIA-AA on diagnostic guidelines. In order to diagnose MCI due to AD the formal cognitive test was used and the threshold was set at the $4^{th}$ percentile or below (standard deviation is less than 1.5) of a scale score derived from subjects of the same age and educational level. The experiments of the present invention aimed to explore diagnostic parameters capable of identifying subjects from groups of healthy individuals, MCI due to AD, or AD dementia according to the results of plasma amyloid and tau-protein assays.

All of the participants or their primary caregivers provided informed consent prior to participating in this investigation.

Experimental Details

Three kinds of reagents (MF-AB0-0060, MF-AB2-0060, MF-TAU-0060, MagQu) were used for assaying the biomarkers of Aβ-40, Aβ-42, and tau protein, respectively. Each kind of reagent was consisted of magnetic nanoparticles dispersed in a pH-7.2 phosphoryl buffer solution (PBS). These reagents were prepared by immobilizing antibodies against Aβ-40 (sc-53822, Santa Cruz Biotech), Aβ-42 (437900, Invitrogen), and tau protein (Tau-441, Sigma) respectively on magnetic nanoparticles. The mean diameter of antibody-functionalized magnetic nanoparticles was 50-60 nm. The magnetic concentration of each kind of reagent was 12 mg-Fe/ml.

The volumes of reagents and to-be-detected samples used for the measurements of IMR signals are summarized in Table I. Each mixture was put into a SQUID-based alternative-current (ac) magnetosusceptometer (XacPro-S, MagQu)

to detect the time dependent ac magnetic susceptibility. After antibody-functionalized magnetic nanoparticles had associated with target biomarkers, the ac magnetic susceptibility of the mixture reduced. The reduction in the magnetic susceptibility was referred as the IMR signal.

TABLE I

Volumes of reagents and plasma used for the detections of IMR signals

| Biomarker | Volume of reagent | Volume of plasma |
|---|---|---|
| Aβ-40 | 80 ml | 40 ml |
| Aβ-42 | 60 ml | 60 ml |
| Tau protein | 80 ml | 40 ml |

In this experiment several solutions with various concentrations of Aβ-40/Aβ-42/tau protein were prepared. These solutions were used as to-be-detected samples to establish the relationships between the IMR signal and Aβ-40/Aβ-42/tau protein. These relationships were referred as characteristic curves. Then, IMR signals of human plasma for Aβ-40, Aβ-42, and tau protein were detected and converted to the concentrations of Aβ-40, Aβ-42, and tau protein by the characteristic curves. The demographic characteristics of 66 healthy individuals (healthy controls), 24 patients with MCI due to AD (mild cognitive impairment due to Alzheimer's disease, MCI), and 31 patients with very mild and 30 patients with mild-to-serve AD dementia (ADD) are listed in Table II.

TABLE II

Demographic characteristics of subjects

| Group | HC | MCI | ADD |
|---|---|---|---|
| Numbers | 66 | 24 | 61 |
| Female/Male | 32/34 | 12/12 | 28/33 |
| Age (years old) | 23-81 | 55-95 | 53-89 |

HC: healthy controls; MCI: mild cognitive impairment due to Alzheimer's disease; ADD: Alzheimer's disease dementia including those with very mild to severe (CDR = 0.5 to 3) dementia.

Results and Discussion

Figure 3:
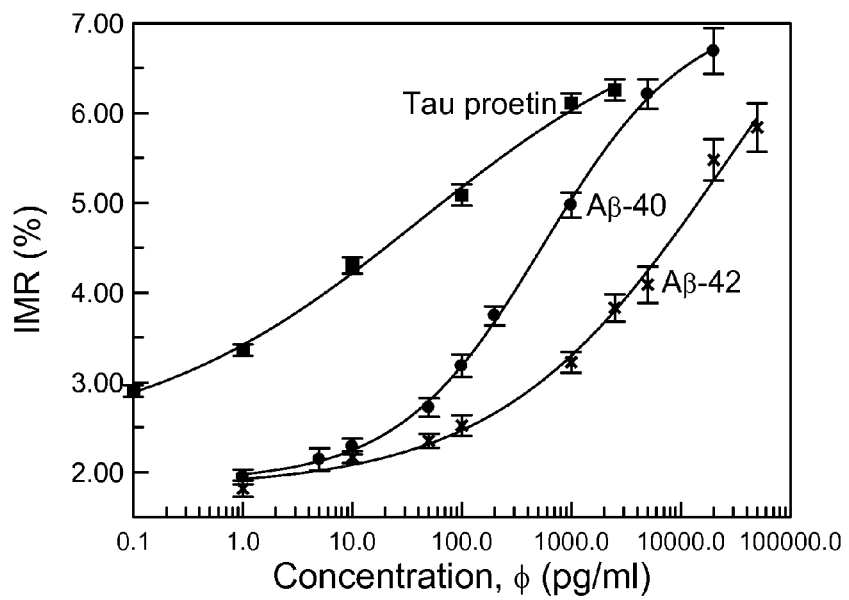
FIG. 3 shows the concentration-dependent IMR signal curve with error bars. (●) denotes Aβ-40, (X) denotes Aβ-42 and (■) denotes tau protein.

The concentration-dependent IMR signals, i.e. IMR (%)-ϕ curves or characteristic curves, for Aβ-40, Aβ-42, and tau protein spiked in PBS are shown with data points in FIG. 3. For a given biomarker, the data points were well fitted with the logistic function (I):

$$IMR(\%) = \frac{A - B}{1 + \left(\frac{\phi}{\phi_o}\right)^\gamma} + B \qquad (I)$$

Wherein, A, B, $\phi_o$, and $\gamma$ were fitting parameters, fitting parameter A was the background value, B was the maximum value, $\phi_o$ was the concentration of the biomarker when the IMR signal equals ((A+B)/2), and $\gamma$ was the slope at data point $\phi_o$ of a curve where $\phi$ was x-axis and IMR(%) was y-axis of the curve. The corresponding parameters for Aβ-40, Aβ-42 and tau protein, listed in Table III, were calculated by fitting data points to the logistic function (I). The fitting curves in FIG. 3 were plotted in solid lines. The lowest detection limits for Aβ-40, Aβ-42 and tau protein assays were down to a level of pg/ml.

TABLE III

Fitting parameters in logistic function (I) for Aβ-40, Aβ-42, and tau protein.

| Biomarker | A | B | $\phi_o$ | $\gamma$ |
|---|---|---|---|---|
| Aβ-40 | 1.89 | 7.39 | 567.3 | 0.65 |
| Aβ-42 | 1.91 | 8.09 | 14157.7 | 0.49 |
| Tau protein | 2.28 | 7.34 | 39.03 | 0.33 |

Figure 4:
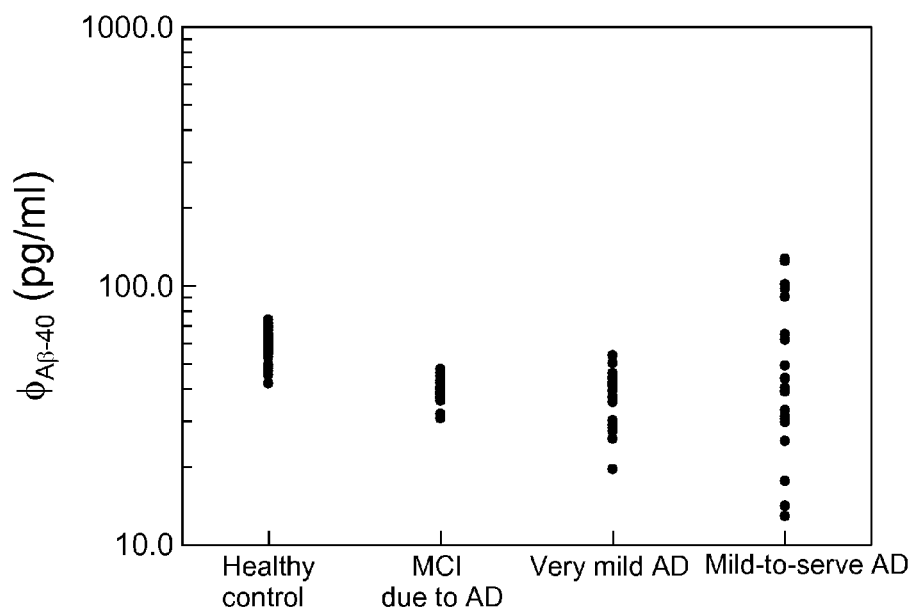
FIG. 4 shows the concentrations of plasma Aβ-40 protein detected by Aβ-40 reagent aided IMR assays in various clinical groups.

The Aβ-40 concentrations $\phi_{A\beta-40}$ of human plasma were measured by using SQUID IMR. The results were shown in FIG. 4. It was found that there was no significant difference in $\phi_{A\beta-40}$ among healthy controls, MCI due to AD, very mild AD Dementia and mild to serve AD Dementia groups. This result implied Aβ-40 in plasma was not a useful biomarker for diagnosing MCI or AD. This was also true for the concentrations of Aβ-40 of the CSF samples from the patients with AD Dementia.

Figure 5:
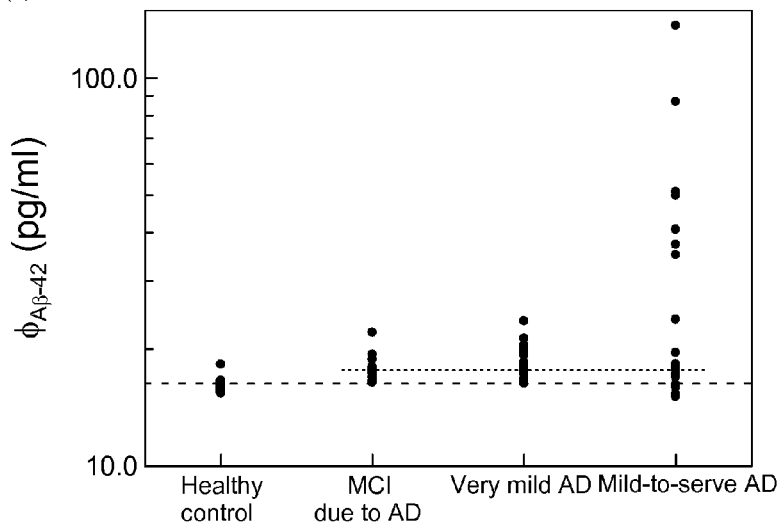
FIG. 5 (a) shows the concentrations of plasma Aβ-42 protein detected by Aβ-42 reagent aided IMR assays in various clinical groups. (b) shows a ROC curve which is capable of differentiating a group of healthy subjects from a patient group (including mild cognitive impairment due to Alzheimer's disease (MCI due to AD), mild Alzheimer's disease (AD) and moderate to severe Alzheimer's disease dementia (ADD). (c) shows a ROC curve which is capable of differentiating a group of patients suffering from MCI due to AD from a group of patients suffering from ADD.
Figure 5:
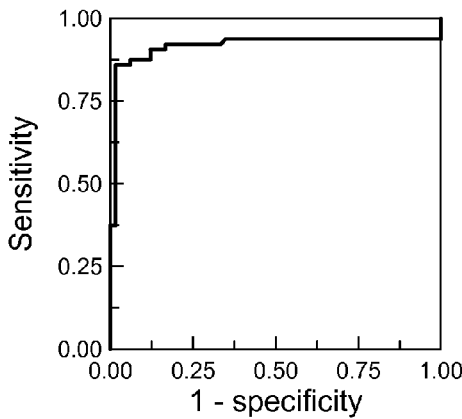
Figure 5:
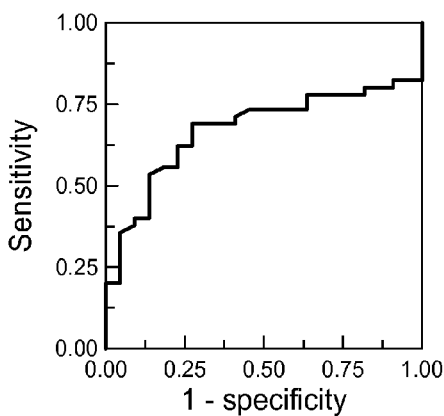

As for Aβ-42, the detected concentrations $\phi_{A\beta-42}$ in plasma were shown in FIG. 5 (a). The concentrations of Aβ-42 for the healthy controls were relatively low as compared with those of the patients with MCI due to AD and AD Dementia groups. This observation was opposite to the results for the reduction in Aβ-42 concentration reported in CSF samples usually measured by using enzyme-linked immunosorbent assay (ELISA). The reasons for the contrast could be several folds such as changes in permeability of blood brain barrier to amyloids in patients with Alzheimer's disease and extra-brain sources of plasma amyloids. As for the different results, the decreased or no change of plasma Aβ-42 concentrations, reported in some of the previous studies, was probably caused by the iron-chelating effect of magnetic $Fe_3O_4$ nanoparticles in the reagent, which prevented oligomerization of Aβ-42 peptide in plasma. As compared to other studies, the concentration of Aβ-42 detected by using IMR in this experiment was relatively higher in the MCI and AD groups.

To further characterize the diagnostic properties, MCI due to AD, very mild AD, and mild-severe AD groups were combined into one group, the patient group. Receiver operating characteristic (ROC) curve analysis was shown in FIG. 5 (b), the threshold in terms of Aβ-42 concentration between the healthy control group and the patient group was 16.33 pg/ml, which was presented in dashed line in FIG. 5 (a). As shown in FIG. 5 (b), when Aβ-42 concentration in plasma was used to differentiate the healthy controls from patients suffering from MCI and dementia due to AD, the sensitivity and specificity were 0.91 and 0.88, respectively. The specificity and sensitivity for differentiating MCI from dementia due to AD in the patient group were further examined. The ROC curve shown in FIG. 5 (c) revealed that the sensitivity and specificity were 0.69 and 0.68, respectively, the threshold was 17.65 pg/ml, which was presented as dotted line in FIG. 5 (a). All the results of threshold, sensitivity, and specificity were listed in Table IV.

TABLE IV

Thresholds, sensitivity, and specificity for differentiating healthy controls, MCI due to AD and AD dementia of various parameters

| Parameter | Groups | Threshold | Sensitivity | Specificity |
|---|---|---|---|---|
| $\phi_{A\beta-42}$ | HC vs. Patients | 16.33 pg/ml | 0.91 | 0.88 |
| | MCI vs. ADD | 17.65 pg/ml | 0.69 | 0.68 |

TABLE IV-continued

Thresholds, sensitivity, and specificity for differentiating healthy controls, MCI due to AD and AD dementia of various parameters

| Parameter | Groups | Threshold | Sensitivity | Specificity |
|---|---|---|---|---|
| $\phi_{Tau}$ | HC vs. Patients | 23.89 pg/ml | 0.97 | 0.91 |
| | MCI vs. ADD | 37.93 pg/ml | 0.74 | 0.79 |
| $\phi_{A\beta-42} \times \phi_{Tau}$ | HC vs. Patients | 455.49 (pg/ml)$^2$ | 0.96 | 0.97 |
| | MCI vs. AD | 642.58 (pg/ml)$^2$ | 0.77 | 0.83 |

HC: healthy controls; MCI: mild cognitive impairment due to Alzheimer's disease; ADD: Alzheimer's disease dementia including those with very mild to severe (CDR = 0.5 to 3) dementia; combine ADD and MCI to form Patients.

Figure 6:
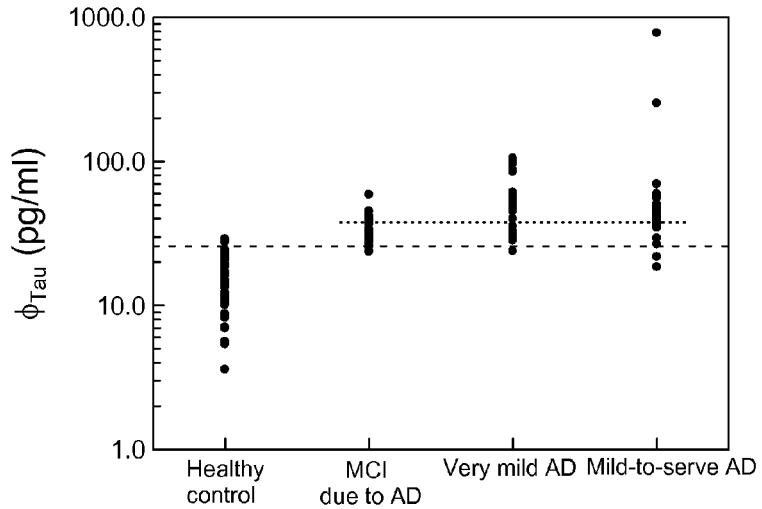
FIG. 6 (a) shows the concentration of plasma tau protein detected by using IMR assays in various clinical groups. (b) shows a ROC curve which is capable of differentiating a group of healthy subjects from a patient group (including MCI due to AD, mild AD, and moderate to severe ADD. (c) shows a ROC curve which is capable of differentiating a group of patients suffering from MCI due to AD and a group of patients suffering from ADD.
Figure 6:
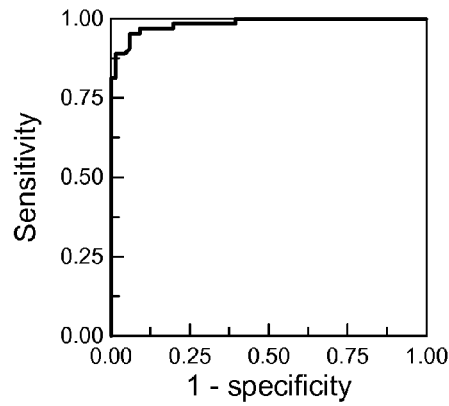
Figure 6:
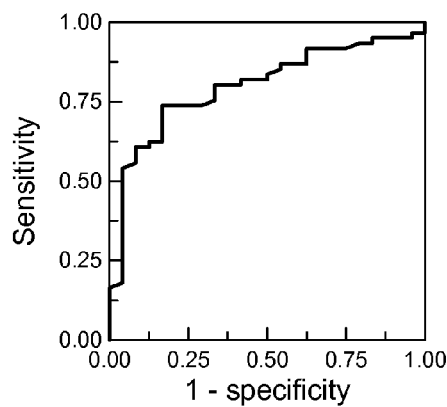

FIG. 6(a) shows the concentrations $\phi_{Tau}$ of plasma tau protein in different clinical groups. A clear cut-off threshold of 23.89 pg/ml was observed between the healthy controls and the patient group. The specificity and sensitivity were 0.97 and 0.91, respectively as shown in FIG. 6 (b). The threshold of 23.89 pg/ml for tau-protein concentration was shown as the dashed line in FIG. 6 (a). The increase in plasma tau-protein concentrations of the MCI and AD groups were consistent with the increase in CSF tau-protein concentration reported in many of the previous reports. In the patient group, the ROC curves of the MCI due to AD group and the AD dementia group were further analyzed. The ROC curve was shown in FIG. 6 (c), the sensitivity was 0.74, the specificity was 0.79 and the threshold was 37.93 pg/ml. The threshold 37.93 pg/ml for tau-protein concentration between the MCI group and the AD group was shown as the dotted line in FIG. 6 (a).

The results shown in FIGS. 5 (a) and 6 (a) suggested that Aβ-42 and tau protein in plasma exhibited high sensitivity and specificity for identifying patients with either MCI or AD. Recent studies and researches reported that Aβ-42 protein was indeed a biomarker of Alzheimer's disease with high specificity. However, tau protein was a biomarker with low specificity because its concentration increased whenever there was a brain damage. Therefore, tau protein concentration was not suitable to determine the severity of Alzheimer's disease.

Figure 7:
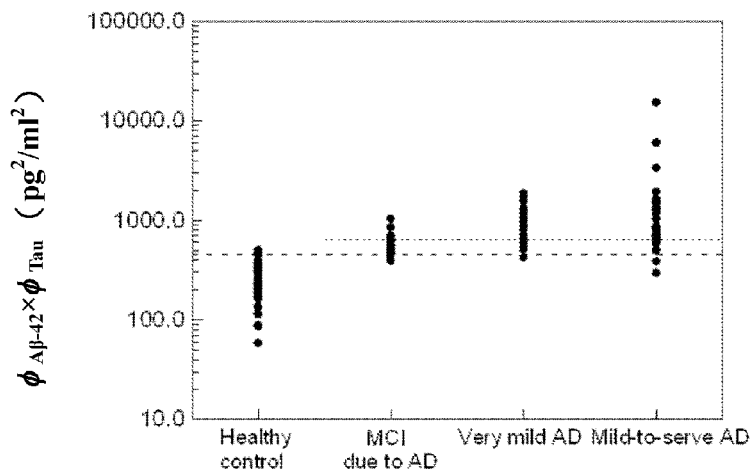
FIG. 7 (a) shows the product of plasma Aβ-42 protein concentration and plasma tau protein concentration detected in various clinical groups by using IMR assays. (b) shows a ROC curve which is capable of differentiating a group of healthy subjects and a patient group (including MCI due to AD, mild AD, and moderate to severe ADD. (c) shows a ROC curve which is capable of differentiating a group of patients suffering from MCI due to AD and a group of patients suffering from ADD.
Figure 7:
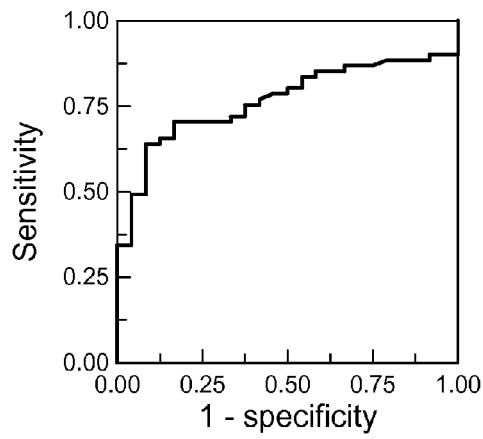
Figure 7:
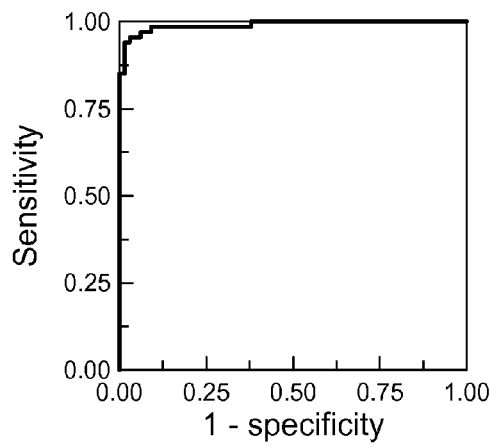

In order to differentiate MCI due to AD from AD dementia a better parameter should be sought. Since concentrations of both Aβ-42 and tau protein were higher in the patient group as compared to those of the healthy controls, it was reasonable to propose the product of Aβ-42 and tau-protein concentrations as a potential diagnostic parameter to differentiate AD dementia from MCI due to AD. The concentration product of Aβ-42 and tau protein for the MCI due to AD group, AD dementia group (including very mild AD and mild-to-severe AD), and healthy controls were shown in FIG. 7 (a). ROC analysis identified a threshold of 642.58 (pg/ml)$^2$ which could be used to differentiate MCI due to AD from AD dementia, the sensitivity was 0.77, the specificity was 0.83. The product of Aβ-42 concentration and tau-protein concentration performed better in differentiating MCI due to AD from AD dementia than using Aβ-42 concentration or tau-protein concentration alone. The concentration product yielded a higher accuracy and could be applied to improve the diagnosis of the patient group. As shown in FIG. 7 (c), based on ROC curve analysis the sensitivity was 0.96, the specificity was 0.97 and the threshold was 455.49 (pg/ml)$^2$. The results shown in FIGS. 7 (a)-(c) revealed that the concentration product of Aβ-42 and tau protein in plasma was a better diagnostic parameter as compared to individual biomarker of either Aβ-42 or tau protein.

Instead of individual biomarker such as Aβ-42 or tau protein, the concentration product of plasma Aβ-42 and plasma tau protein improved the sensitivity and specificity of AD diagnosis and was capable of differentiating MCI due to AD from AD dementia with sensitivity of 0.77 and specificity of 0.83. In addition to its accuracy, another advantage of the Alzheimer's disease diagnostic method disclosed by the present invention was that it used plasma samples rather than CSF samples. The safety and accessibility of the assay was significantly enhanced by utilizing SQUID IMR. Therefore, the experiment proved that the SQUID IMR assay on plasma biomarkers was a promising diagnostic aid not only to detect AD dementia but also to identify MCI at the preclinical stage of AD.

What is claimed is:

1. A method for detecting the risk of Alzheimer's disease of a patient suffering from mild cognitive impairment (MCI), comprising:

(a) detecting in vitro immunomagnetic reduction (IMR) signals of two Alzheimer's disease biomarkers in a blood sample of the patient, wherein the IMR signals are produced by the two Alzheimer's disease biomarkers binding with magnetic nanoparticles containing an anti-Alzheimer's disease biomarker antibody, wherein the two Alzheimer's disease biomarkers are tau protein and Aβ-42 protein;

(b) fitting the IMR signals of the two Alzheimer's disease biomarkers detected in step (a) to a logistic function (I) to calculate each Alzheimer's disease biomarker's concentration in the biological sample:

$$IMR(\%) = \frac{A - B}{1 + \left(\frac{\phi}{\phi_o}\right)^\gamma} + B \quad (I)$$

wherein IMR(%) is the IMR signals of the Alzheimer's disease biomarkers, $\phi$ is the concentration of the Alzheimer's disease biomarker, fitting parameter A is a background value, B is a maximum value, $\phi_0$ is the concentration of the biomarker when IMR signal equals $((A+B)/2)$, $\gamma$ is a slope at data point $\phi_0$ of a curve where $\phi$ is x-axis and IMR(%) is y-axis; and (c) comparing the product of the two Alzheimer's disease biomarkers' concentration obtained in step (b) to a predetermined threshold which is the product of two Alzheimer's disease biomarkers' concentrations calculated by using a receiver operating characteristic (ROC) curve, when the product of two Alzheimer's disease biomarkers' concentrations is higher than the predetermined threshold, the increased risk of Alzheimer's disease of the patient is identified.

2. The method of claim 1, wherein the predetermined threshold is determined by a data point of the highest specificity at the highest sensitivity on the ROC curve.

3. The method of claim 1, wherein the predetermined threshold is determined by the maximum area under the ROC curve.

4. The method of claim 1, wherein the ROC curve is plotted according to the products of the two Alzheimer's disease biomarkers' concentrations of subjects from both an Alzheimer's disease patient group and a MCI patient group.

5. The method of claim 1, wherein the material of the magnetic nanoparticles is selected from the group consisting of $Fe_3O_4$, $Fe_2O_3$, $MnFe_2O_4$, $CoFe_2O_4$ and $NiFe_2O_4$.

6. The method of claim 1, wherein the material of the magnetic nanoparticles is $Fe_3O_4$.

7. The method of claim 1, wherein the blood sample is plasma.

\* \* \* \* \*